United States Patent
Kuduvalli et al.

(10) Patent No.: US 8,086,004 B2
(45) Date of Patent: Dec. 27, 2011

(54) USE OF A SINGLE X-RAY IMAGE FOR QUALITY ASSURANCE OF TRACKING

(75) Inventors: Gopinath Kuduvalli, San Jose, CA (US); Dongshan Fu, Santa Clara, CA (US); Calvin R. Maurer, Jr., Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 745 days.

(21) Appl. No.: 12/199,293

(22) Filed: Aug. 27, 2008

(65) Prior Publication Data
US 2009/0180678 A1 Jul. 16, 2009

Related U.S. Application Data

(60) Provisional application No. 61/011,331, filed on Jan. 15, 2008.

(51) Int. Cl.
*G06K 9/00* (2006.01)
(52) U.S. Cl. ........................................ 382/128
(58) Field of Classification Search .................. 382/128
See application file for complete search history.

(56) References Cited

U.S. PATENT DOCUMENTS

| | | | |
|---|---|---|---|
| 6,326,963 B1 | 12/2001 | Meehan | |
| 6,496,598 B1 | 12/2002 | Harman | |
| 6,867,773 B2 | 3/2005 | Hux | |
| 7,227,925 B1 * | 6/2007 | Mansfield et al. | 378/65 |
| 2002/0049375 A1 | 4/2002 | Strommer et al. | |
| 2004/0015073 A1 * | 1/2004 | Schell et al. | 600/411 |
| 2006/0050847 A1 * | 3/2006 | Jaffray et al. | 378/65 |
| 2007/0071176 A1 | 3/2007 | Main et al. | |
| 2007/0127845 A1 | 6/2007 | Fu | |
| 2007/0274577 A1 | 11/2007 | De Font-Reaulx-Rojas | |
| 2008/0130825 A1 | 6/2008 | Fu et al. | |
| 2011/0107270 A1 * | 5/2011 | Wang et al. | 715/850 |

OTHER PUBLICATIONS

Tang, et al., Fiducial Registration from a Single X-Ray Image: A New Techniquie for Fluoroscopic Guidance and Radiotherpy, S.L. Delp. A.M. DiGiogia, and B. Jaramaz (Eds.): MICCAI2000, LNCS 1935, pp. 502-511, 2000.*
Rhode, et al., Registration and Tracking to Integrate X-Ray and MR Images in an XMR Facility, IEEE Transactions on Medical Imaging, vol. 22, No. 11, Nov. 2003.*
Supplementary European Search Report for European Patent Application No. 08870643.7, dated Dec. 10, 2010.
Dongshan Fu et al., "Xsight Lung Tracking System: A Fiducial-Less Method for Respiratory Motion Tracking", Jan. 1, 2007, Treating Tumors That Move With Respiration, Springer, DE, pp. 265-282, XP009142170, ISBN: 978-3-540-69885-2.
Yelin Suh et al., "Geometric uncertainty of 2D projection imaging in monitoring 3D tumor motion", Physics in Medicine and Biology, Taylor and Francis Ltd. London, GB, vol. 52, No. 12, Jun. 21, 2007, pp. 3439-3454, XP020112919, ISSN: 0031-9155.

(Continued)

*Primary Examiner* — Rodney Fuller
(74) *Attorney, Agent, or Firm* — Lowenstein Sandler PC

(57) ABSTRACT

A method and system for aligning a volume of interest in a three-dimensional treatment coordinate system with a reference position using stereoscopic imaging data and for monitoring and correcting alignment of the volume of interest in the three-dimensional treatment coordinate system using monoscopic imaging data.

30 Claims, 12 Drawing Sheets

OTHER PUBLICATIONS

Khamene A. et al., "Automatic registration of portal images and volumetric CT for patient positioning in radiation therapy", Medical Image Analysis, Oxford University Press, Oxofrd, GB, vol. 10, No. 1, Feb. 1, 2006, pp. 96-112, XP025154071, ISSN: 1361-8415.

Zhiping Mu et al., "Multiple Fiducial Identification Using the Hidden Markov Model in Image Guided Radiosurgery", Computer Vision and Pattern Recognition Workshop, 2006 Conference on New York, NY, USA Jun. 17-22, 2006, Piscataway, NJ, USA, IEEE, Piscataway, NJ, USA, Jun. 17, 2006, pp. 92-92, XP010922904.

BrainLAB: "IGRT ExacTrac® Brochure", Oct. 15, 2007, XP002613785, URL: http://web.archive.org/web/20071015153601/www.brainlab.com/download/pdf/IGTExacTracBrochure.pdf. [retrieved on Dec. 10, 2010.

Ross I. Berbeco, Steve B. Jiang, Gregory C. Sharp, George T Y Chen, Hassan Mostafavi, Hiroki Shirato, "Integrated radiotherapy imaging system (IRIS): design considerations of tumour tracking with linac gantry-mounted diagnostic x-ray systems with flat-panel detectors", Institute of Physics Publishing, Physics in Medicine and Biology, PH: S0031-9155(04)68365-5, Phys. Med. Biol. 49 (2004) pp. 243-255.

PCT International Search Report and Written Opinion of the International Searching Authority, PCT/US08/13644 filed Dec. 11, 2008, mailed Mar. 20, 2009.

* cited by examiner

USE OF A SINGLE X-RAY IMAGE FOR QUALITY ASSURANCE OF TRACKING

REFERENCE TO RELATED APPLICATION

This application claims the benefit of the filing date of U.S. Provisional Patent Application No. 61/011,331 filed Jan. 15, 2008, which is incorporated herein by reference in its entirety.

TECHNICAL FIELD

Embodiments of the present invention are related to the field of image-guided systems and, in particular, to image-guided radiation treatment systems.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a linear accelerator (LINAC) to generate x-rays. In one type of external beam radiation therapy, an external radiation source directs a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to and from the tumor. As a result, the cumulative radiation dose at the tumor is high and the average radiation dose to healthy tissue is low.

The term "radiosurgery" refers to a procedure in which radiation is applied to a target region at levels that are sufficient to necrotize a pathology. Radiosurgery is typically characterized by relatively high radiation doses per treatment (e.g., 1000-2000 centiGray), extended treatment times (e.g., 45-60 minutes per treatment) and hypo-fractionation (e.g., one to three days of treatment). The term "radiotherapy" refers to a procedure in which radiation is applied to a target region for therapeutic, rather than necrotic, purposes. Radiotherapy is typically characterized by a low dose per treatment (e.g., 100-200 centiGray), shorter treatment times (e.g., 10 to 30 minutes per treatment) and hyper-fractionation (e.g., 30 to 45 days of treatment). For convenience, the term "radiation treatment" is used herein to encompass both radiosurgery and radiotherapy unless otherwise noted.

Image-guided radiation treatment (IGRT) systems include gantry-based systems and robot-based systems. In gantry-based systems, the radiation source is attached to a gantry that moves around a center of rotation (isocenter) in a single plane. The radiation source may be rigidly attached to the gantry or attached by a gimbaled mechanism. Each time a radiation beam is delivered during treatment, the axis of the beam passes through the isocenter. Treatment locations are, therefore, limited by the rotation range of the radiation source, the angular range of the gimbaled mechanism and the degrees of freedom of a patient positioning system. In robot-based systems, such as the CYBERKNIFE® system, developed by Accuray Incorporated of Sunnyvale, Calif., the radiation source is not constrained to a single plane of rotation and has five or more degrees of freedom.

In conventional image-guided radiation treatment systems, patient tracking during treatment is accomplished by comparing two-dimensional (2D) in-treatment x-ray images of the patient to 2D digitally reconstructed radiographs (DRRs) derived from three dimensional (3D) pre-treatment diagnostic imaging data of the patient. The pre-treatment imaging data may be computed tomography (CT) data, cone-beam CT, magnetic resonance imaging (MRI) data, positron emission tomography (PET) data or 3D rotational angiography (3DRA), for example. Typically, the in-treatment x-ray imaging system is stereoscopic, producing images of the patient from two or more different points of view (e.g., orthogonal projections).

A DRR is a synthetic x-ray image generated by casting (mathematically projecting) rays through the 3D imaging data, simulating a known geometry of the in-treatment x-ray imaging system. The resulting DRR then has the same scale and point of view as the in-treatment x-ray imaging system, and can be compared with the in-treatment x-ray images to determine the position and orientation of the patient (and the radiation target within the patient). Different patient poses are simulated by performing 3D transformations (rotations and translations) on the 3D imaging data before each DRR is generated.

Each comparison of an in-treatment x-ray image with a DRR produces a similarity measure or, equivalently, a difference measure, which can be used to search for a 3D transformation that produces a DRR with a higher similarity measure to the in-treatment x-ray image. Similarity measures may be intensity-based or feature-based (e.g., using internal or external fiducial markers or natural anatomical features such as the spine or skull). When the similarity measure is sufficiently maximized (or equivalently, a difference measure is minimized), the corresponding 3D transformation can be used to align the patient in the radiation treatment system so that the actual treatment conforms to the treatment plan.

Conventionally, these treatment systems require two stereoscopic in-treatment x-ray images to insure that the patient is properly positioned in the 3D coordinates of the treatment system before the treatment is started, and these images are acquired periodically during the treatment session. As noted above, the positioning of the radiation treatment source follows a plan that is designed to achieve a target radiation dose to the pathological anatomy, while limiting the radiation dose to critical structures and other healthy tissue. If the treatment plan does not account for the geometry of the in-treatment imaging system, the radiation treatment source may block one of the x-ray imaging beam paths and interfere with stereoscopic imaging.

Conventionally, in order to verify the patient position, the gantry or robot, respectively, must be moved to clear the blocked line of sight of the imaging system, and then be moved back to apply the treatment beam. This procedure wastes time and prolongs the patient's time in the operating theater.

In other situations, the radiation treatment source may not be blocking an imaging path, but one of the two stereoscopic images may not be useable for patient tracking. For example, fiducial markers or anatomical landmarks (e.g., bony structures such as the skull or spine) may be visible in only one of the images. In another example, intensity variations in one of the two images may be too low to guarantee a high quality similarity measure for pattern intensity matching.

BRIEF DESCRIPTION OF THE DRAWINGS

The present invention is illustrated by way of example, and not by way of limitation, in the figures of the accompanying drawings, in which.

DETAILED DESCRIPTION

Figure 1:
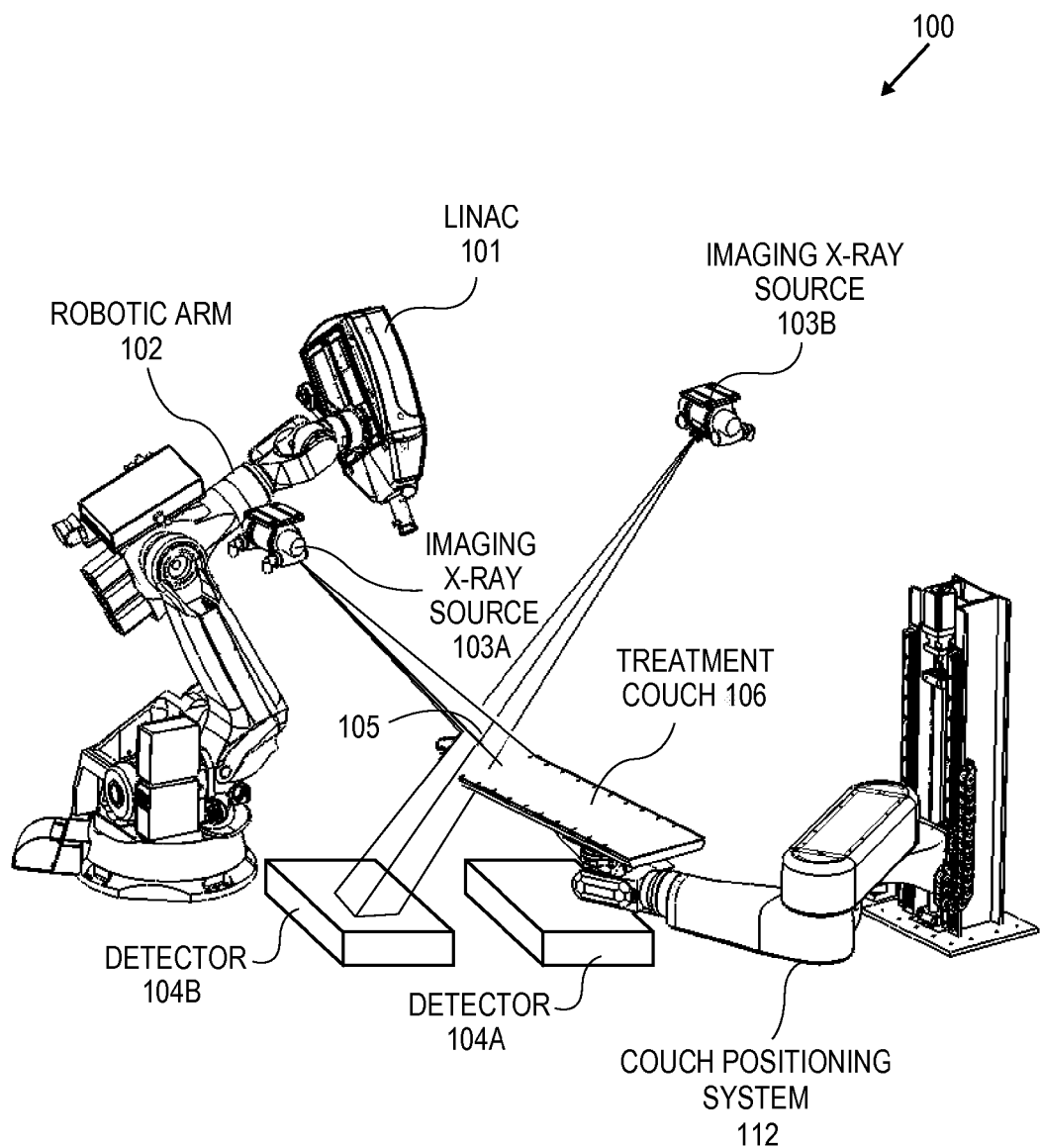
FIG. 1 illustrates a robotic treatment delivery system.

Described herein is a method and system for aligning a volume of interest in a 3D treatment coordinate system with a reference position using stereoscopic imaging data and for monitoring and correcting alignment of the volume of interest in the 3D treatment coordinate system using monoscopic imaging data. In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention.

Unless stated otherwise as apparent from the following discussion, it will be appreciated that terms such as "generating," "registering," "determining," "aligning," "positioning," "processing," "computing," "selecting," "estimating," "comparing," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

In general, two stereoscopic images are used to perform 2D to 2D registration to align a VOI with a reference position, to directly track a tumor with the images, and/or to check the validity of and to update a correlation model. However, at times, one of the images of the stereo imaging pair may not be usable. For example, the radiation treatment source may block one of the x-ray imaging beam paths, a robotic arm of the radiation treatment source or of the treatment couch may block one of the x-ray imaging beam paths, fiducial markers or anatomical landmarks may be visible in only one of the images, or the intensity variations in one of the two images be too low to guarantee a high quality similarity measure for pattern intensity matching. When one of the images of the stereo imaging pair is not usable, the embodiments described herein may use the monoscopic imaging data for quality assurance purposes.

In one embodiment, the monoscopic imaging data may be used to perform 2D to 2D registration of the available image with the corresponding DRR. This registration may be an intensity-based registration, or a point-based registration (e.g., fiducial tracking). If the 2D registration with the one image indicates that the patient (or the region of interest in the patient anatomy) has not been displaced by more than a pre-set threshold with respect to the previously determined position, then the treatment can proceed using the corrections for the displacement from the previous image.

In another embodiment, while the tumor is tracked directly with the images, bony structures, for example, may be visible in one of the two projections and the bony structure cannot be kept in the field of view at the same time in both images. In this embodiment, the available image can be used to perform tracking in 2D to determine if a re-alignment is necessary.

The embodiments described herein may also be used in other applications, such as to acquire only the one image by modeling the motion of the radiation treatment source to determine if one of the images is blocked for a particular position, minimizing the x-ray exposure to the patient.

FIG. 1 illustrates the configuration of an image-guided, robot-based radiation treatment system 210, such as the CYBERKNIFE® system, developed by Accuray Incorporated of Sunnyvale, Calif., that may be used to implement embodiments of the present invention. In FIG. 1, the radiation treatment source is a linear accelerator (LINAC) 101 mounted on the end of a robotic arm 102 having multiple (e.g., 5 or more) degrees of freedom in order to position the LINAC 101 to irradiate a pathological anatomy (target region or volume) with beams delivered from many angles, in many planes, in an operating volume around the patient.

The treatment delivery system of FIG. 1 includes an in-treatment imaging system, which may include x-ray sources 103A and 103B and x-ray detectors (imagers) 104A and 104B. The two x-ray sources 103A and 103B may be mounted in fixed positions on the ceiling of an operating room and may be aligned to project imaging x-ray beams from two different angular positions (e.g., separated by 90 degrees) to intersect at an imaging isocenter 105 (which provides a reference point for positioning the patient on a treatment couch 106 during treatment using a couch positioning system 112) and to illuminate imaging planes of respective detectors 104A and 104B after passing through the patient. In other embodiments of the present invention, system 100 may include more or less than two x-ray sources and more or less than two detectors, and any of the detector-source pairs may be movable rather than fixed. In yet other embodiments of the present invention, the positions of the x-ray sources and the detectors may be interchanged.

Figure 2:
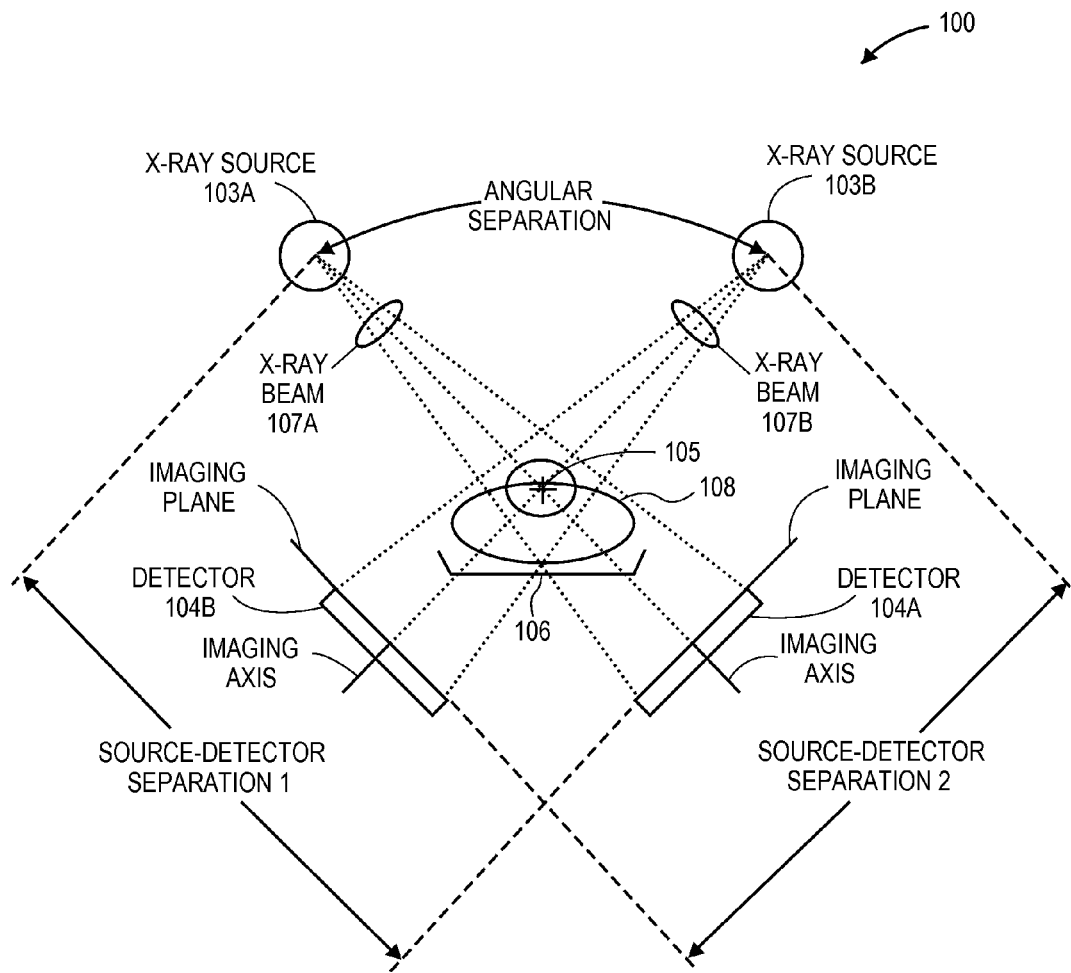
FIG. 2 illustrates the geometry of an imaging system in one embodiment of the present invention.

FIG. 2 is a partial schematic representation of system 100 illustrating the imaging geometry of system 100. In FIG. 2, the x-ray sources 103A and 103B are separated by an angular separation for stereoscopic imaging of a volume of interest (VOI) in a patient 108 on treatment couch 106. The x-ray sources 103A and 103B project x-ray beams 107A and 107B, respectively, though a patient 108 onto the respective imaging detectors 104A and 104B. Each detector is characterized by an imaging plane and an imaging axis. The point where the imaging axes cross defines the imaging isocenter 105. The locations of the imaging planes define a source-to-detector separation for each of the source-detector pairs.

The x-ray detectors 104A and 104B periodically capture two-dimensional (2D) projection images of the VOI in the patient 108. Whenever the radiation treatment source 101 is not blocking one of the imaging paths, and the quality of the images is good enough, these 2D projection images of the VOI in the two projections provide stereoscopic imaging data. The stereo imaging data from the pair of x-ray images in stereo geometry may be used to determine the displacement (e.g., six degrees of freedom displacement) of the patient anatomy or the tumor with respect to the desired position with reference to the 3D scan data. In one embodiment, the stereoscopic imaging data may be used to align the VOI in the treatment room coordinate system with a reference position of the VOI defined by 3D scan data of the VOI. Alignment may be achieved by registering the 2D projection images in each of the two projections with DRRs derived from 3D transformation of the 3D scan data. As noted above, a DRR is a synthetic x-ray image, generated from 3D image data that simulates the imaging geometry of the treatment delivery system. Different patient poses in the treatment delivery system can be simulated by performing 3D transformations (rotations and translations) on the 3D imaging data before each DRR is generated. Alternatively, DRR's corresponding to these 3D transformations (rotations and translations) can be generated by modifying the projection geometry (e.g., treatment room coordinate system) to correspond to the 3D transformations, thus, eliminating the need for transformation of the 3D imaging data before DRR generation. It should be noted that, although in physical space the treatment room and imaging systems are fixed, conceptually in software, the treatment room coordinate system and imaging system may be represented virtually and the relative transformations may be performed on either the 3D imaging data or the treatment coordinate system (e.g., stereoscopic projection imaging system) relative to the patient (e.g., VOI). The two transformations would be inverses of each other.

Registration is the determination of a one-to-one mapping, or transformation, between the coordinates in one space and those in another space, such that points in the two spaces (volume elements, or "voxels" in the case of volume image data) that correspond to the same anatomical point are mapped to each other. Once the correct 3D transformation is found, the volume of interest may be moved (translated and rotated) through the inverse of the 3D transformation, by a positioning system, to match the reference position of the 3D scan data. Alternatively, the 3D transformation may be entered as a correction factor in the positioning plan of a radiation treatment source (e.g., LINAC 101). Alternatively, some combination of a movement of the VOI through a portion of the inverse transformation and a partial correction of the positioning plan of the radiation treatment source may be used.

In a stereoscopic imaging system, registration may be performed by comparing 2D projection images of a VOI (e.g., x-ray images), in each of two (or more) projections, with 2D reference images of the VOI (e.g., DRRs) in each of the projections. Each comparison of a pair of x-ray images with a pair of DRRs produces similarity measures or, equivalently, difference measures, which can be used to search for a 3D transformation that produces a pair of DRRs that maximizes the similarity measure. When the similarity measure is maximized (or the difference measure is minimized), the corresponding 3D transformation can be used to align the VOI in the treatment coordinate system with the reference position corresponding to the treatment plan.

Figure 3:
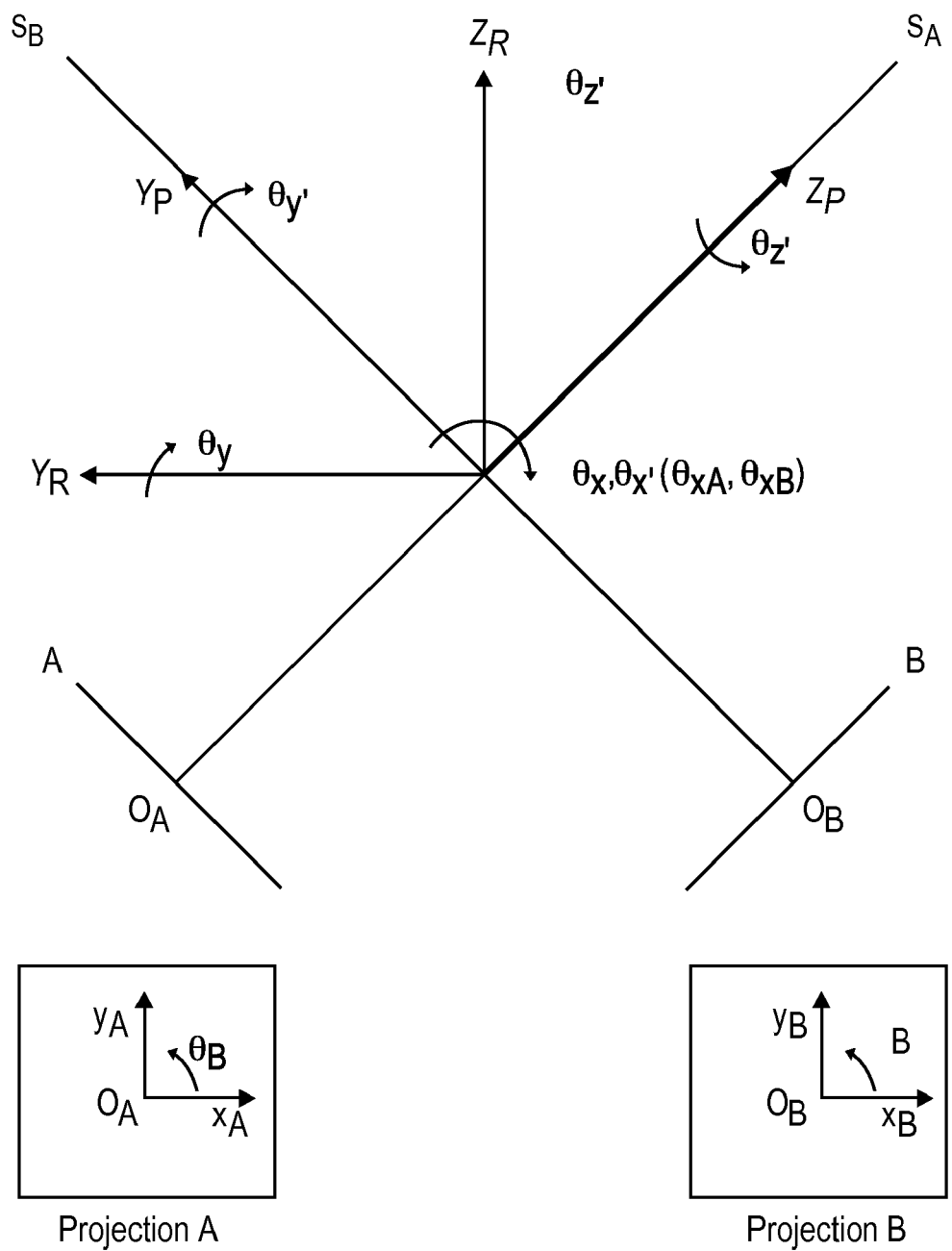
FIG. 3 illustrates the 3D transformations between an in-treatment coordinate system and a reference coordinate system.
Figure 4A:
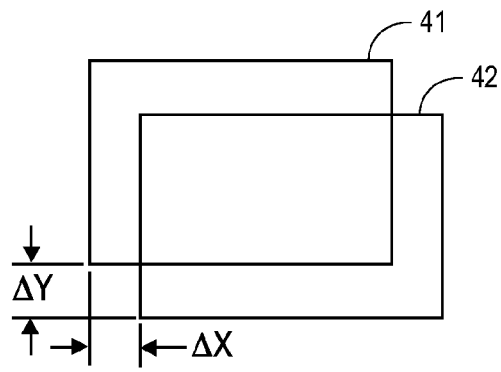
FIG. 4A illustrates in-plane translation in one embodiment of the present invention.
Figure 4B:
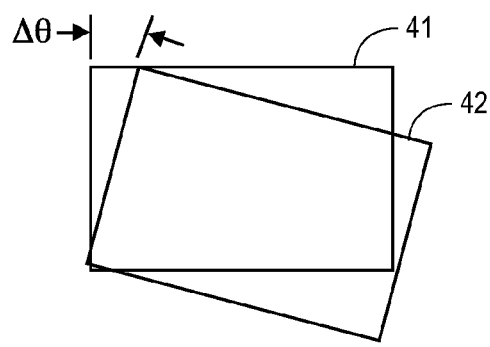
FIG. 4B illustrates in-plane rotation in one embodiment of the present invention.
Figure 4C:
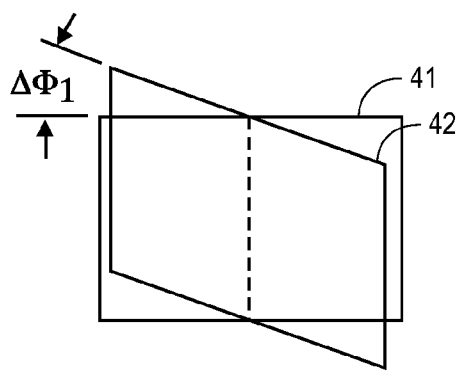
FIG. 4C illustrates a first out-of-plane rotation in one embodiment of the present invention.
Figure 4D:
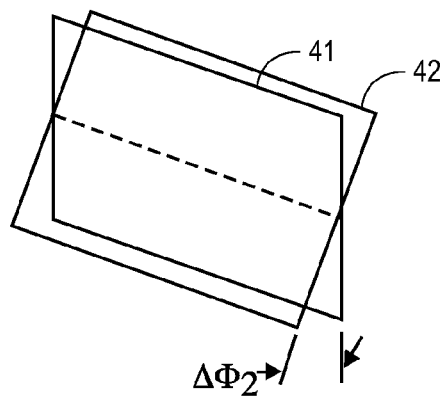
FIG. 4D illustrates a second out-of-plane rotation in one embodiment of the present invention.

FIG. 3 illustrates 3D transformation parameters between the 3D coordinates $[X_P, Y_P, Z_P]$ of a VOI in an imaging system having two 2D projections A and B, and a 3D reference coordinate system $[X_R, Y_R, Z_R]$ associated with 3D scan data of the patient (in FIG. 3, the x-coordinates of both coordinate systems are normal to, and pointing into the plane of FIG. 3). Projections A and B in FIG. 3 are associated with the positions of detectors 104A and 104B in imaging system 100, $S_A$ and $S_B$ represent the positions of x-ray sources 103A and 103B, and $O_A$ and $O_B$ are the centers of the imaging planes of the x-ray detector in the two positions (i.e., where the imaging axes intersect the imaging planes). In FIG. 3, the projections A and B are viewed from the directions $O_A S_A$ and $O_B S_B$, respectively. These two 2D image projections are compared against DRRS to achieve image registration and alignment, both for global patient alignment and for target tracking. In the example of FIG. 3, the angular separation of the two source-detector positions is shown as 90 degrees for ease of illustration, and the following equations are derived for this configuration. Other imaging geometries are possible and the corresponding equations may be derived in a straightforward manner by one of ordinary skill in the art.

A 3D transformation may be defined from coordinate system $[X_P, Y_P, Z_P]$ (having coordinates x',y',z') to coordinate system $[X_R, Y_R, Z_R]$ (having coordinates x,y,z) in FIGS. 4A-4D in terms of six parameters: three translations ($\Delta x, \Delta y, \Delta z$) and three rotations ($\Delta\theta_x, \Delta\theta_y, \Delta\theta_z$). A 3D rigid transformation between the two 3D coordinate systems can be derived from basic trigonometry as:

$$x=x', \ y=(y'-z')/\sqrt{2}, \ z=(y'+z')/\sqrt{2},$$

$$\theta_x=\theta_{x'}, \ \theta_y=(\theta_{y'}-\theta_{z'})/\sqrt{2}, \ \theta_z=(\theta_{y'}+\theta_{z'})/\sqrt{2}. \quad (1)$$

In the 2D coordinate system $(x_A, y_A)$ for projection A, the 3D rigid transformation may be decomposed into an in-plane transformation ($\Delta x_A, \Delta y_A, \Delta\theta_A$) and two out-of-plane rotations ($\Delta\theta_{x_A}, \Delta\theta_{y_A}$). Similarly, in the 2D coordinate system $(x_B, y_B)$ for projection B, the decomposition is comprised of the in-plane transformation ($\Delta x_B, \Delta y_B, \Delta\theta_B$) and two out-of-plane rotations ($\Delta\theta_{x_B}, \Delta\theta_{z_B}$). FIGS. 4A through 4D illustrate the in-plane transformations and out-of-plane rotations described herein, where a 2D x-ray image is represented by plane 41 and the 2D DRR is represented by plane 42. The 3D rigid transformation of equation (1) may be simplified by noting that the use of two projections over-constrains the solution to the six parameters of the 3D rigid transformation. The translation $x_A$ in projection A is the same parameter as $x_B$ in projection B, and the out-of-plane rotation $\theta_{x_A}$ in projection A is the same as $\theta_{x_B}$ in projection B. If $\alpha_A$ and $\alpha_B$ are geometric amplification factors (e.g., scale factors related to source-to-patient and patient-to-detector distances) for projections A and B, respectively, then the translations between the coordinate system [x'y'z'] and the 2D coordinate systems have the following relationships:

$$\Delta x'=(\alpha_B \Delta x_B - \alpha_A \Delta x_A)/2, \ \Delta y'=\alpha_A \Delta y_A, \ \Delta z'=\alpha_B \Delta y_B. \quad (2)$$

For projection A, given a set of DRR images that correspond to different combinations of the two out-of-plane rotations ($\Delta\theta_{x_A},\Delta\theta_{y'}$), the 2D in-plane transformation ($\Delta x_A,\Delta y_A,\Delta\theta_A$) may be estimated by a 2D to 2D image comparison, and the two out-of-plane rotations ($\Delta\theta_{x_A},\Delta\theta_{y'}$) may be calculated by matching the image to the set of DRR images as described below, using similarity measures. Likewise, the same process may be used to solve the 2D in-plane transformation ($\Delta x_B,\Delta y_B,\Delta\theta_B$) and the out-of-plane rotations ($\Delta\theta_{x_B},\Delta\theta_{z'}$) for the projection B. As described below, the in-plane transformation and out-of-plane rotations may be obtained by registration between the image and a DRR, independently for both projection A and projection B. When a DRR image with a matching out-of-plane rotation is identified, the in-plane rotation and the out-of-plane rotation have the following relationships:

$$\Delta\theta_{y'}=\Delta\theta_B, \Delta\theta_{z'}=\Delta\theta_A. \quad (3)$$

If the out-of-plane rotation $\theta_{y'}$ is ignored in the set of reference DRR images for projection A, the in-plane transformation can be approximately described by ($\Delta x_A,\Delta y_A,\Delta\theta_A$) when $\theta_{y'}$ is small (e.g., less than 5 degrees). Once this simplifying assumption is made, and given a set of reference DRR images which correspond to various out-of-plane rotations $\Delta\theta_{x_A}$, the in-plane transformation ($\Delta x_A,\Delta y_A,\Delta\theta_A$) and the out-of-plane rotation $\Delta\theta_{x_A}$ may be found by one or more search methods as are known in the art. These methods generally employ the calculation of a similarity measure, followed by the application of a gradient search algorithm to maximize the similarity between the in-treatment x-ray images and selected DRRs. Examples of similarity measures include (but are not limited to) normalized cross-section, entropy of the difference image, mutual information, gradient correlation, pattern intensity and gradient difference. A corresponding simplification may be made for projection B.

Given the results ($\Delta x_A,\Delta y_A,\Delta\theta_A,\Delta\theta_{x_A}$) in projection A and ($\Delta x_B,\Delta y_B,\Delta\theta_B,\Delta\theta_{x_B}$) in projection B, the approximation of the 3D rigid transformation in the 3D image coordinate system may be obtained using the following expressions:

$$\Delta x = (-\alpha_A \Delta x_A + \alpha_B \Delta x_B)/2, \Delta y = (\alpha_A \Delta y_A - \alpha_B \Delta y_B)/\sqrt{2}, \Delta z = (\alpha_A \Delta y_A + \alpha_B \Delta y_B)/\sqrt{2},$$

$$\Delta\theta_x = (\Delta\theta_{x_A}+\Delta\theta_{x_B})/2, \Delta\theta_y = (\Delta\theta_B - \Delta\theta_A)/\sqrt{2}, \Delta\theta_z = (\Delta\theta_B + \Delta\theta_A)/\sqrt{2}. \quad (4)$$

Thus, the six-parameter, 3D transformation required to align the 3D coordinate system of the imaging system with the 3D coordinate system of a 3D scan volume may be completely defined by the two sets of four parameters ($\Delta x_A,\Delta y_A,\Delta\theta_A,\Delta\theta_{x_A}$) and ($\Delta x_B,\Delta y_B,\Delta\theta_B,\Delta\theta_{x_B}$).

Other ways of determining transformations as are known in the art are contemplated in one or more embodiments of the present invention. In one embodiment of the present invention, the 2D x-ray images in each projection of the x-ray imaging system may be combined for direct 2D-3D registration with the pre-operative 3D scan data as described in U.S. Patent Publication No. US 2007/0127845.

It will be apparent from the foregoing discussion that, in general, two stereoscopic images are required to align a VOI with a reference position using 2D projection images of the VOI and DRRs of the VOI. However, in various embodiments of the present invention, described below, monoscopic imaging data (i.e., a single 2D projection image) may be used in conjunction with a DRR in the same projection to verify the alignment of a VOI, and to detect movement of the VOI after an initial stereoscopic alignment. For example, in radiation treatment systems that use bone structures to perform to perform intensity-based registration (e.g. the XSIGHT® tracking systems and 6D Skull Tracking System, developed by Accuray Incorporated of Sunnyvale, Calif.), one of the 2D projections may have a low sensitivity to patient movement after an initial patient alignment. Low sensitivity may arise, for example, from a patient position that foreshortens or distorts the 2D projection of bone features. However, the other 2D projection may have a sufficient level of sensitivity to verify the patient's position and to detect patient movement. In other embodiments of the present invention, the monoscopic imaging data may be used to correct a detected misalignment of the VOI after an initial stereoscopic alignment.

In some radiation treatment applications, a target pathology (e.g., a lung tumor) may be tracked directly with the two 2D projections, but the spinal structures that are used for global patient alignment may appear in only one projection (e.g., the distance between the tumor and the spinal features may prevent both from appearing in the field of view of both projections). As described above, the projection containing a usable view of the spine may be used to verify alignment or to detect movement.

In one embodiment, the XSIGHT® Lung Tracking system, developed by Accuray Incorporated of Sunnyvale, Calif., performs two sequential registrations, a first global patient alignment by registration of a spine region, then direct tumor tracking by registration of the tumor VOI. Since the spinal region and the lung tumor generally are relatively far apart, it is unlikely to see both the spinal region and the lung tumor in both projection images because the spine structure cannot be kept in the field of view at the same time in both images. If the spine region shows up in only one 2D projection image while tracking the lung tumor, the single 2D projection image (e.g., monoscopic imaging data) may be used to confirm global patient alignment and/or to determine if a re-alignment using the XSIGHT® Lung Tracking system is necessary. Using the single 2D projection image to confirm global patient alignment may prevent the system from returning to the position to image the spine for performing global patient alignment, but may remain at the position to image the lung tumor for direct tumor tracking. Alternatively, the monoscopic imaging data may be used to confirm patient alignment in other tracking systems than the XSIGHT® Lung Tracking system.

Referring again to FIGS. 4A through 4D, a selected DRR and an x-ray image in the same projection would be coincident after an initial stereoscopic alignment. That is, the in-plane translation parameters $\Delta Y$ and $\Delta X$, the in-plane rotation parameter $\Delta\theta$ and the out-of-plane rotation parameters $\Delta\phi_1$ and $\Delta\phi_2$ will all be approximately zero (within the accuracy of the initial alignment process, which may be for example ~0.5 mm). Under this initial condition, certain rotations and translation of the VOI may be monitored and detected using only one projection. As noted above, only one projection may be available due to a blocked imaging path, poor quality in one of the stereoscopic images or a need or desire to limit a patient's total exposure to imaging radiation.

Figure 5:
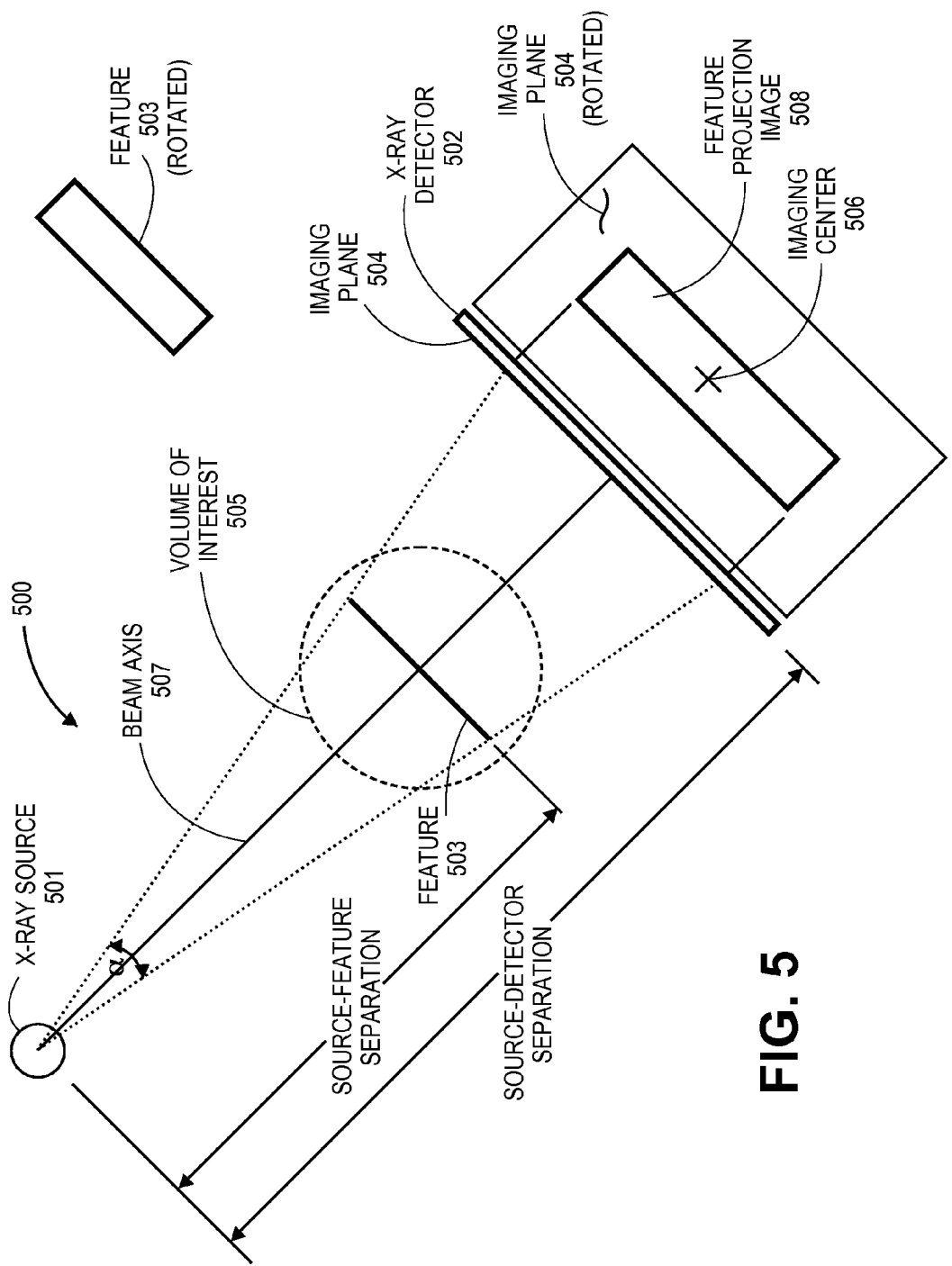
FIG. 5 illustrates a monoscopic imaging system in one embodiment of the present invention.

FIG. 5 illustrates a monoscopic imaging system 500 in one embodiment of the present invention, which may be, for example, either of source-detector pair 103A and 104A or source-detector pair 103B and 104B of imaging system 100. Monoscopic imaging system 500 includes an x-ray source 501 and an x-ray detector 502 having an imaging plane 504 and an imaging center 506 defined by the intersection of beam axis 507 with imaging plane 504. In FIG. 5, it is assumed that a volume of interest 505 includes a feature 503 that can be used for image registration. The feature and the projected image of the feature are illustrated as a simple geometric shape (i.e., a rectangle) for purposes of explanation. In practice, the feature may be a complex shape (e.g., a bone, the skull or a segment of the spine), a pattern of external or implanted fiducial markers or an image intensity pattern.

Feature 503 subtends an angle a, which is a function of the source-feature separation and the size of feature 503. The projected image of feature 503 in imaging plane 504 will be a function of the ratio of the source-detector separation to the source-feature separation.

In one embodiment, the alignment of the VOI in the 3D treatment coordinate system with a reference position using stereoscopic imaging data may be done by 1) acquiring a first 2D projection image of the VOI in each of two or more projections, and 2) registering the first 2D projection image of the VOI in each of the two or more projections with 2D reference images of the VOI in each of the two or more projections. The 2D reference images of the VOI are derived from 3D transformations of 3D scan data of the VOI. The first 2D projection image of the VOI may be registered by 1) comparing the comparing the first 2D projection image in each of the two or more projections with the 2D reference images in each of the two or more projections, 2) determining a first similarity measure between the first 2D projection image in each of the two or more projections and a selected 2D reference image in each of the two or more projections, and 3) finding a first 3D transformation between a coordinate system of the VOI and a coordinate system of the 3D scan data of the VOI that maximizes the first similarity measure. In one embodiment, the first 3D transformation maps voxels in the coordinate system of the VOI to corresponding voxels in the coordinate system of the 3D scan data of the VOI. Alternatively, other types of transformations as would be understood by one of ordinary skill in the art may be used. The VOI can then be moved through an inverse of the first 3D transformation to align the VOI with the reference position. Alternatively, a treatment source can be positioned to compensate for the first 3D transformation.

In one embodiment of the present invention, the alignment of the VOI in the treatment coordinate system may be monitored using the monoscopic imaging data by 1) acquiring a second 2D projection image 508 of feature 503 after the initial stereoscopic alignment (described in the previous embodiment), and 2) comparing the second 2D projection image of the VOI with the DRR used for alignment. Movement of the VOI can be detected by determining a second similarity measure between the second 2D projection image of the VOI and the selected DRR (reference image) of the VOI in one projection, and comparing the second similarity measure to the first similarity measure. If the VOI has moved (i.e., the patient shifts on the treatment couch) after the initial stereoscopic alignment, the second (monoscopic) 2D projection image 508 of feature 503 will differ from the first 2D projection image and produce a second similarity measure which is different from the first similarity measure computed from the 2D projection image used for the initial stereoscopic alignment. If the difference between the second similarity measure and the first similarity measure is below a predetermined value, indicating that the VOI has moved less than a critical amount, then the treatment may then be continued. Detecting movement of the VOI may also include finding a second 3D transformation of the 3D scan data that maximizes the second similarity measure. The VOI can be realigned by moving the VOI through an inverse of the second 3D transformation, or by positioning the treatment source to compensate for the second 3D transformation.

In another embodiment, the alignment of the VOI in the treatment coordinate system may be monitored by 1) acquiring a second 2D projection image 508 of feature 503 after the initial stereoscopic alignment, and 2) comparing the second 2D projection image of the VOI with the first 2D projection image in one of the two or more projections (e.g., one of the pair of x-ray images) in the initial stereoscopic alignment. Like the previous embodiment, movement of the VOI can be detected by determining a second similarity measure between the second 2D projection image and the first 2D projection image. If the VOI has moved (i.e., the patient shifts on the treatment couch) after the initial stereoscopic alignment, the second (monoscopic) 2D projection image 508 of feature 503 will differ from the first 2D projection image and produce a second similarity measure which is different from the first similarity measure computed from the 2D projection image used for the initial stereoscopic alignment. If the difference between the second similarity measure and the first similarity measure is below a predetermined value, indicating that the VOI has moved less than a critical amount, then the treatment may then be continued. Detecting movement of the VOI may also include finding a second 3D transformation of the 3D scan data that maximizes the second similarity measure. The VOI can be realigned by moving the VOI through an inverse of the second 3D transformation, or by positioning the treatment source to compensate for the second 3D transformation. It should be noted that the image-to-image comparison may be better than the image-to-DRR comparison because the DRRs (reference images) tend to have less detail for comparison than the 2D projection image.

FIGS. 6A-6E illustrate how the monoscopic imaging system 500 may be used to detect movement of the VOI after the initial stereoscopic alignment. In FIGS. 6A-6E, the initial (reference) position of feature 503 and feature projection image 508 (corresponding to FIG. 5) are shown as dotted lines, and the new positions are shown as solid lines.

Figure 6A:
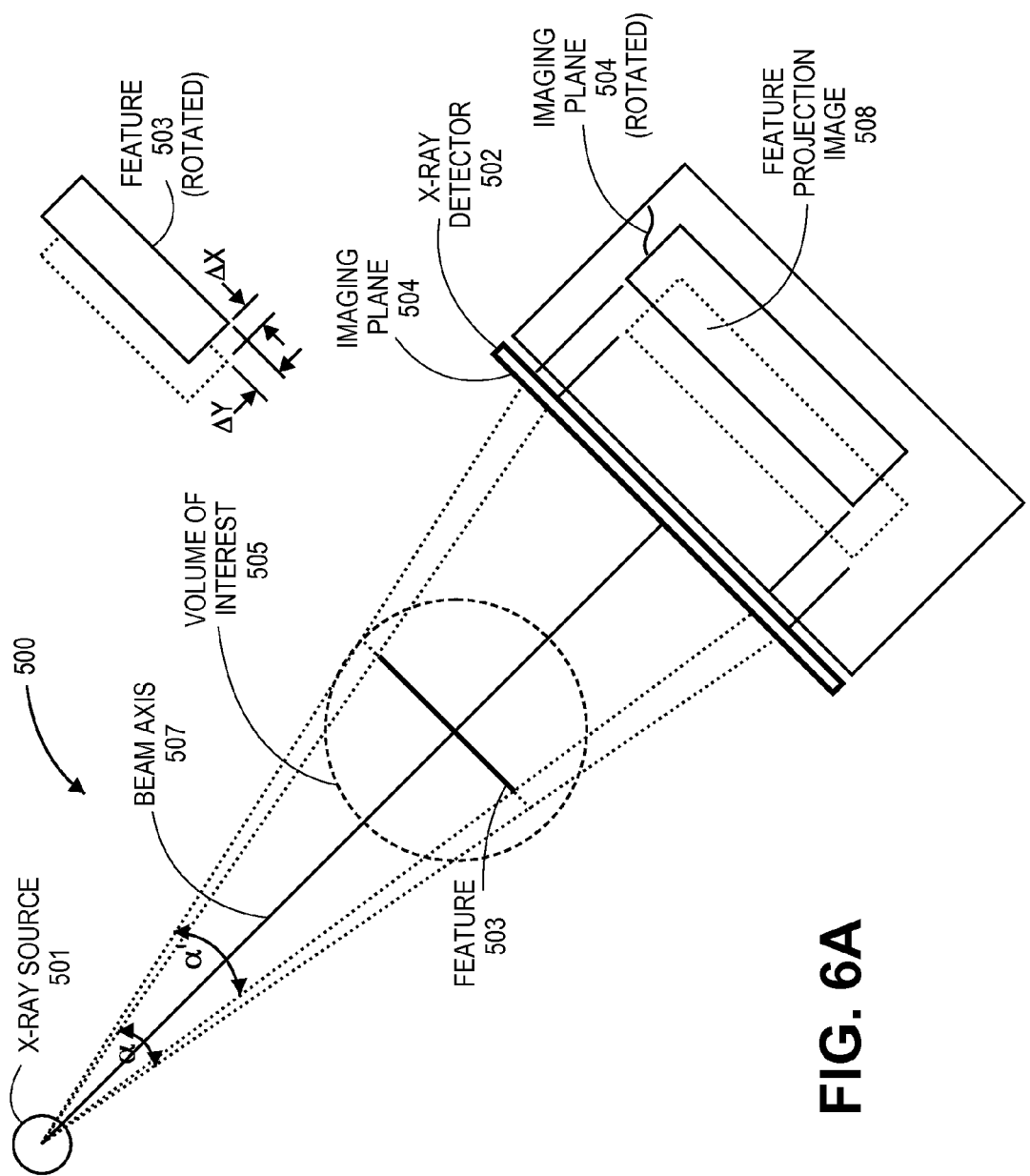
FIG. 6A illustrates in-plane translation in a monoscopic imaging system in one embodiment of the present invention.

FIG. 6A illustrates in-plane translation of the VOI according to one embodiment. As illustrated in FIG. 6A, a movement of the VOI in any combination of X and Y displacements will result in a translation of the feature image 508 in imaging plane 504 that may be compared with the reference position (dotted lines). The translation may be detected as a second similarity measure that differs from the first similarity measure as described above.

Figure 6B:
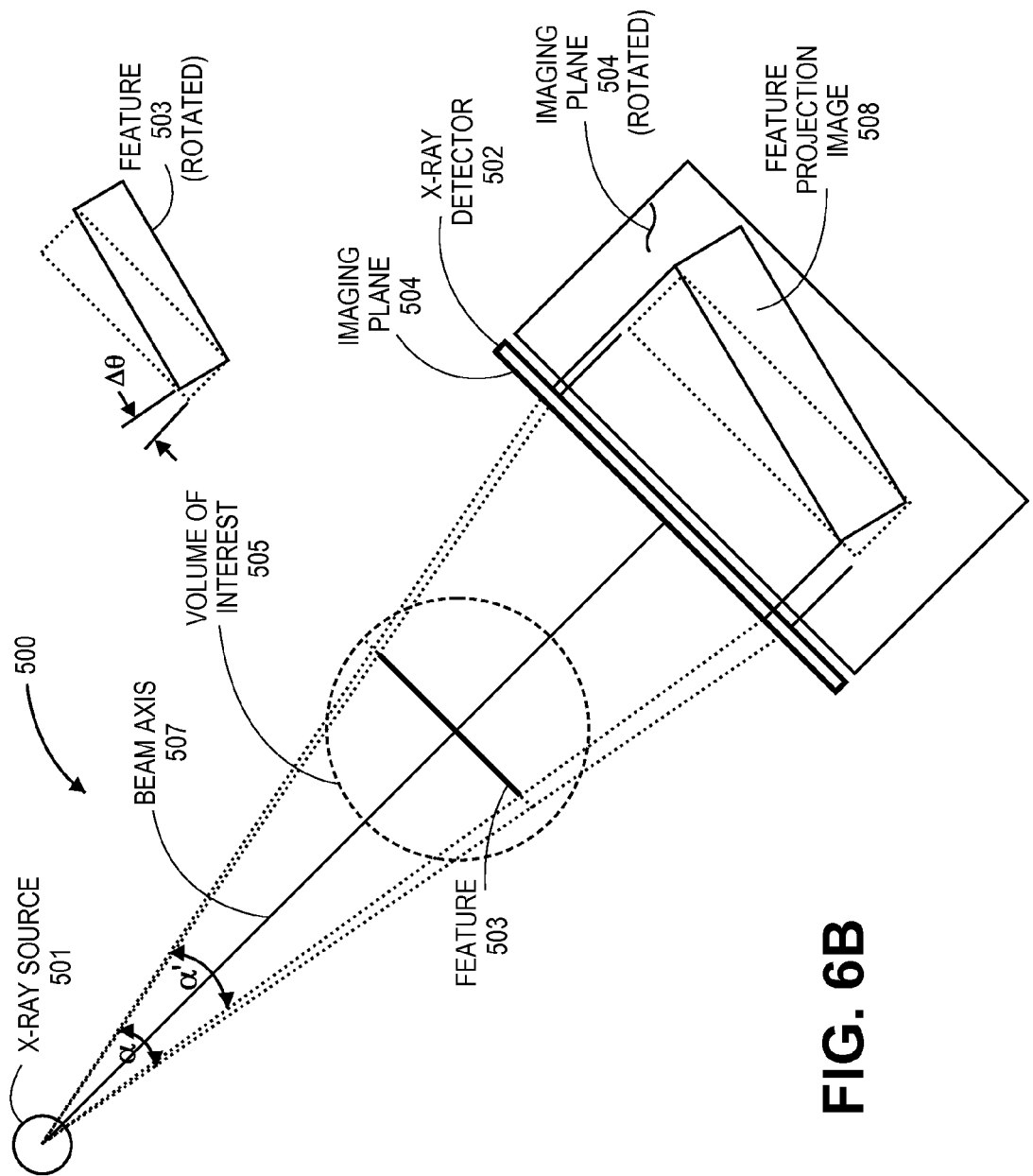
FIG. 6B illustrates in-plane rotation in a monoscopic imaging system in one embodiment of the present invention.

FIG. 6B illustrates in-plane rotation of the VOI according to one embodiment. As illustrated in FIG. 6B, an in-plane rotation of the VOI will result in a rotation of the feature image 508 in imaging plane 504 that may be compared with the reference position. The in-plane rotation may be detected as a second similarity measure that differs from the first similarity measure as described above.

Figure 6C:
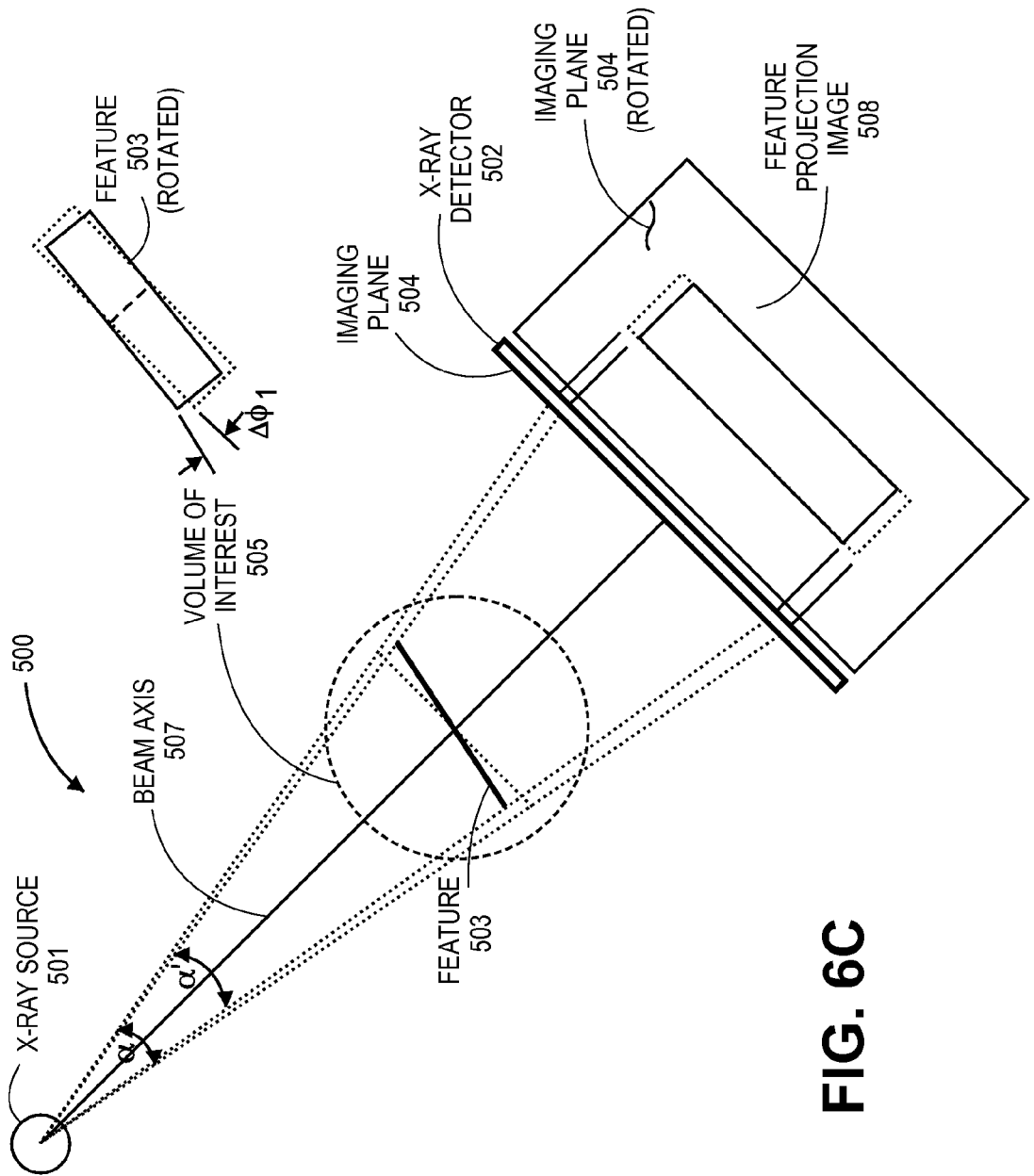
FIG. 6C illustrates a first out-of-plane rotation in a monoscopic imaging system in one embodiment of the present invention.

FIG. 6C illustrates a first out-of-plane rotation of the VOI according to one embodiment. As illustrated in FIG. 6C, the first out-of-plane rotation of the VOI will result in a foreshortening of the feature image 508 in imaging plane 504 in one dimension that may be compared with the reference position. The first out-of-plane rotation may be detected as a second similarity measure that differs from the first similarity measure as described above.

Figure 6D:
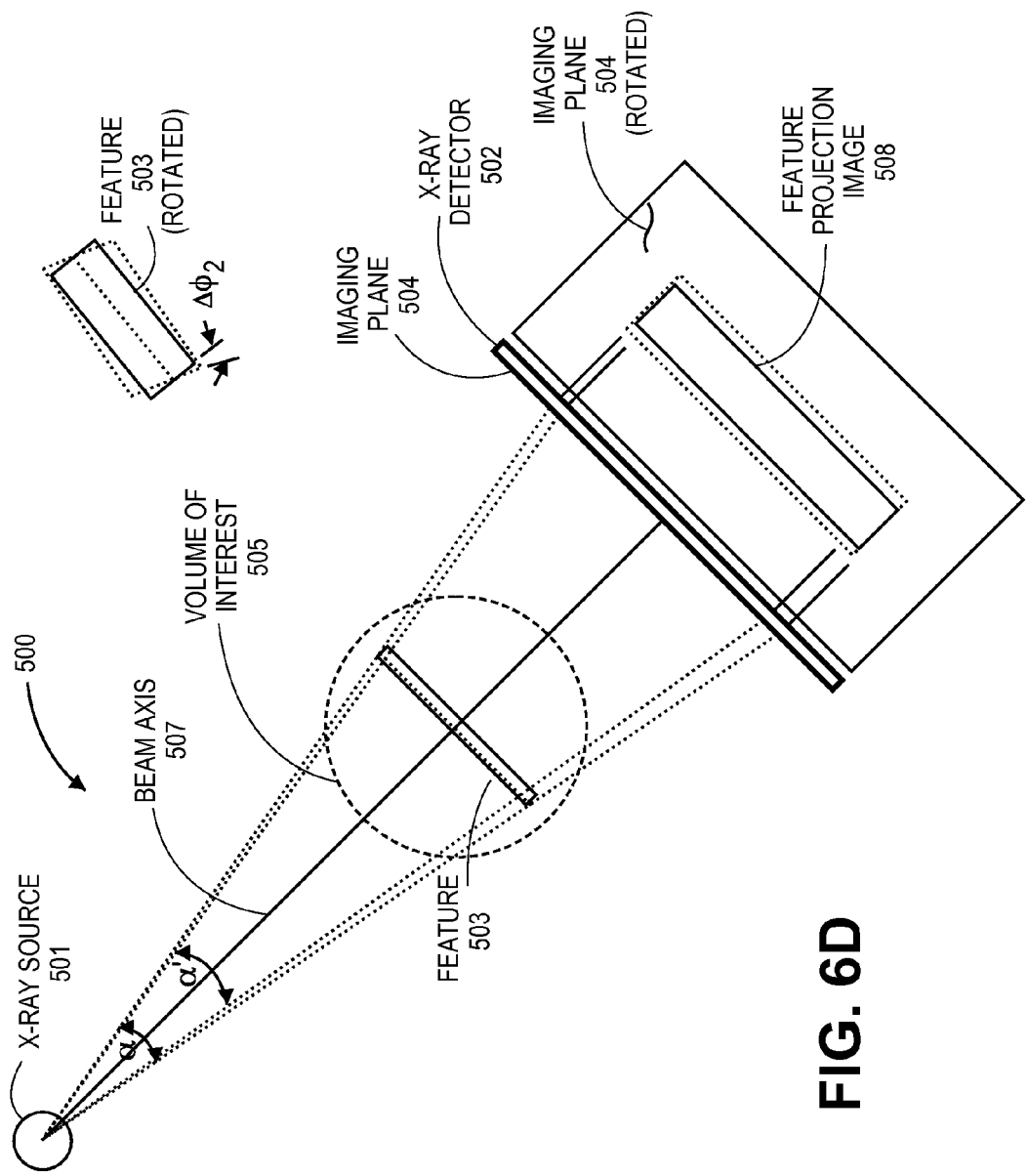
FIG. 6D illustrates a second out-of-plane rotation in a monoscopic imaging system in one embodiment of the present invention.

FIG. 6D illustrates a second out-of-plane rotation of the VOI according to one embodiment. As illustrated in FIG. 6D, the second out-of-plane rotation of the VOI will result in a foreshortening of the feature image 508 in imaging plane 504 in a second dimension that may be compared with the reference position. The second out-of-plane rotation may be detected as a second similarity measure that differs from the first similarity measure as described above.

Figure 6E:
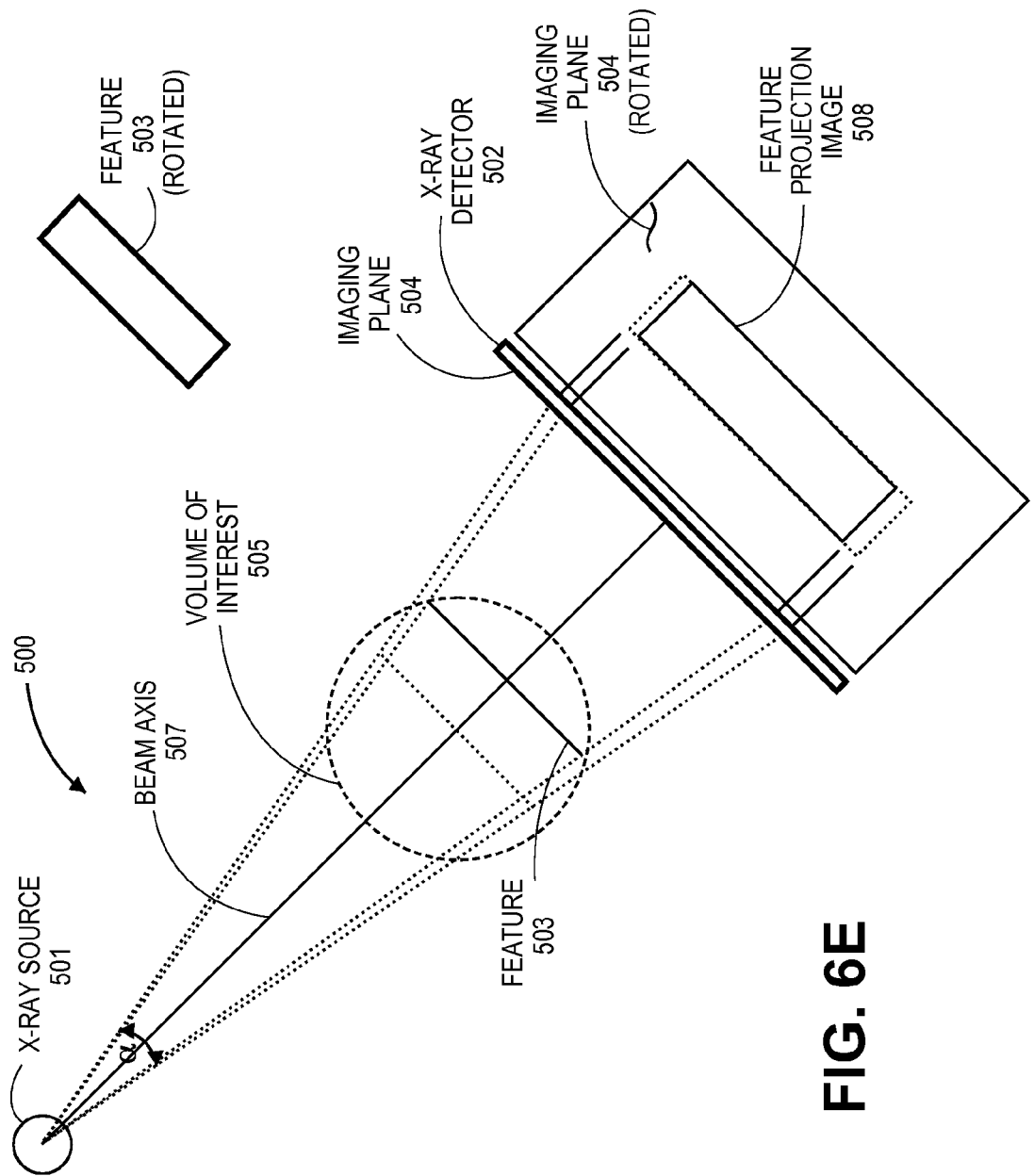
FIG. 6E illustrates an axial translation in a monoscopic imaging system in one embodiment of the present invention.

FIG. 6E illustrates an axial translation of the VOI along the imaging beam axis according to one embodiment. As illustrated in FIG. 6E, if the source and detector are close enough that the imaging beams are not parallel, the translation of the VOI will result in a scaling of the feature image 508 in imaging plane 504 that may be compared with the reference position. The axial translation may be detected as a second similarity measure that differs from the first similarity measure as described above.

In one embodiment of the present invention, if the difference between the second similarity measure and the first similarity measure is less than a first critical value (e.g., a value that indicates that actual radiation dose to the pathological anatomy will differ from the planned dose by less than a maximum amount), then the radiation treatment may be continued, based on the original stereoscopic alignment data (i.e., the 3D transformation between the coordinate system of the VOI and the reference coordinate system of the 3D scan data of the VOI).

In one embodiment of the present invention, if the difference between the second similarity measure and the first similarity measure is greater than or equal to the first critical value, then the radiation treatment may be interrupted until the stereoscopic imaging data can be used to realign the VOI. The monoscopic imaging data may be used to realign the VOI if the monoscopic imaging data is unambiguous. In practice, the imaging data is often not ambiguous. It can be seen from FIGS. 6A and 6B that the directions and magnitudes of in-plane translations and in-plane rotations of the VOI may be distinguished from the monoscopic imaging data. It can be seen from FIG. 6E that the direction and magnitude of axial translations of the VOI may also be distinguished from the monoscopic imaging data. However, the out-of-plane rotations of the VOI, illustrated in FIGS. 6C and 6D, are ambiguous with respect to positive or negative rotation (e.g., a +5 degree rotation is not distinguishable from a −5 degree rotation) because both rotations cast the same 2D projection image. It should be noted that the ambiguity may exist only for symmetric objects. It should also be noted that the embodiments described herein may be used to compute a 6D transformation of a 3D VOI with a single (monoscopic) image as long as the image is a perspective projection image. However, the 6D transformation may be less reliable and less accurate in some dimensions than a pair of stereoscopic images. For example, the depth and out of plane rotation may not be as accurate as in-plane parameters.

If the monoscopic imaging data is not ambiguous, as described above, then the 2D monoscopic projection image of the VOI may be registered with the reference DRR in a manner analogous to the stereoscopic registration described above. The monoscopic projection image may be compared to the reference image (DRR) (or to the first 2D projection image) in the same projection to compute a similarity measure, and the similarity measure may be used to search for a 3D transformation (e.g., combination of in-plane translations and rotations, and axial translations) that maximizes the similarity measure. Then, the VOI may then be moved through the inverse of the 3D transformation, the position of the radiation treatment source may be corrected with the 3D transformation, or some combination of a partial movement and a partial correction may be used as described above.

In one embodiment of the present invention, if the monoscopic imaging data is ambiguous, or if the difference between the second similarity measure and the first similarity measure is greater than or equal to a second critical value (e.g., a value that indicates a level of movement of the VOI that will cause the radiation exposure of critical structures and healthy tissue to exceed a specified maximum), then the radiation treatment may be interrupted until stereoscopic imaging data can be used to realign the VOI.

Figure 7:
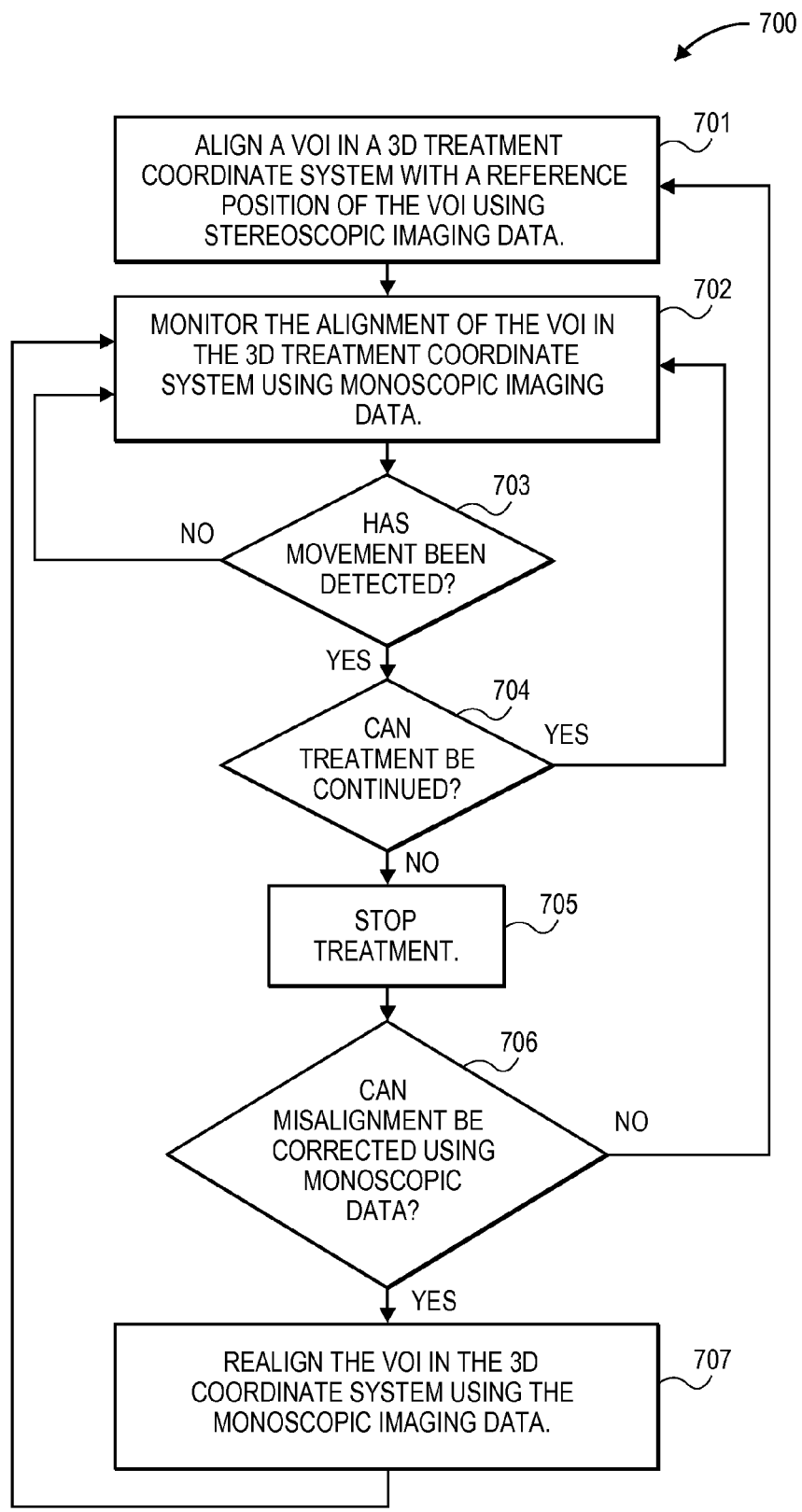
FIG. 7 is a flowchart illustrating a method in one embodiment of the present invention.

FIG. 7 is a flowchart illustrating a method 700 in one embodiment of the present invention. In operation 701, the VOI in a 3D treatment coordinate system is aligned with a reference position of the VOI using stereoscopic imaging data. In operation 702, the alignment of the VOI is monitored using monoscopic imaging data. In operation 703, it is determined if the VOI has moved. If the VOI has not moved, then the method continues at operation 702. If the VOI has moved, then it is determined at operation 704 whether the treatment can be continued without realignment (e.g., if the movement is less than the first critical value). If treatment can be continued, the method continues at operation 702. If the treatment cannot be continued without realignment, then treatment is stopped at operation 705. At operation 706, it is determined if the misalignment can be corrected using monoscopic imaging data (e.g., as described above). If it is determined that the VOI can be realigned using the monoscopic imaging data (e.g., because the movement of the VOI is unambiguous and less than the second critical value), then the VOI is realigned at operation 707 and the method continues at operation 702. If it is determined at operation 706 that the VOI cannot be realigned using the monoscopic imaging data (e.g., because the movement of the VOI is ambiguous or greater than the second critical value), then the method returns to operation 701 for stereoscopic alignment.

Figure 8:
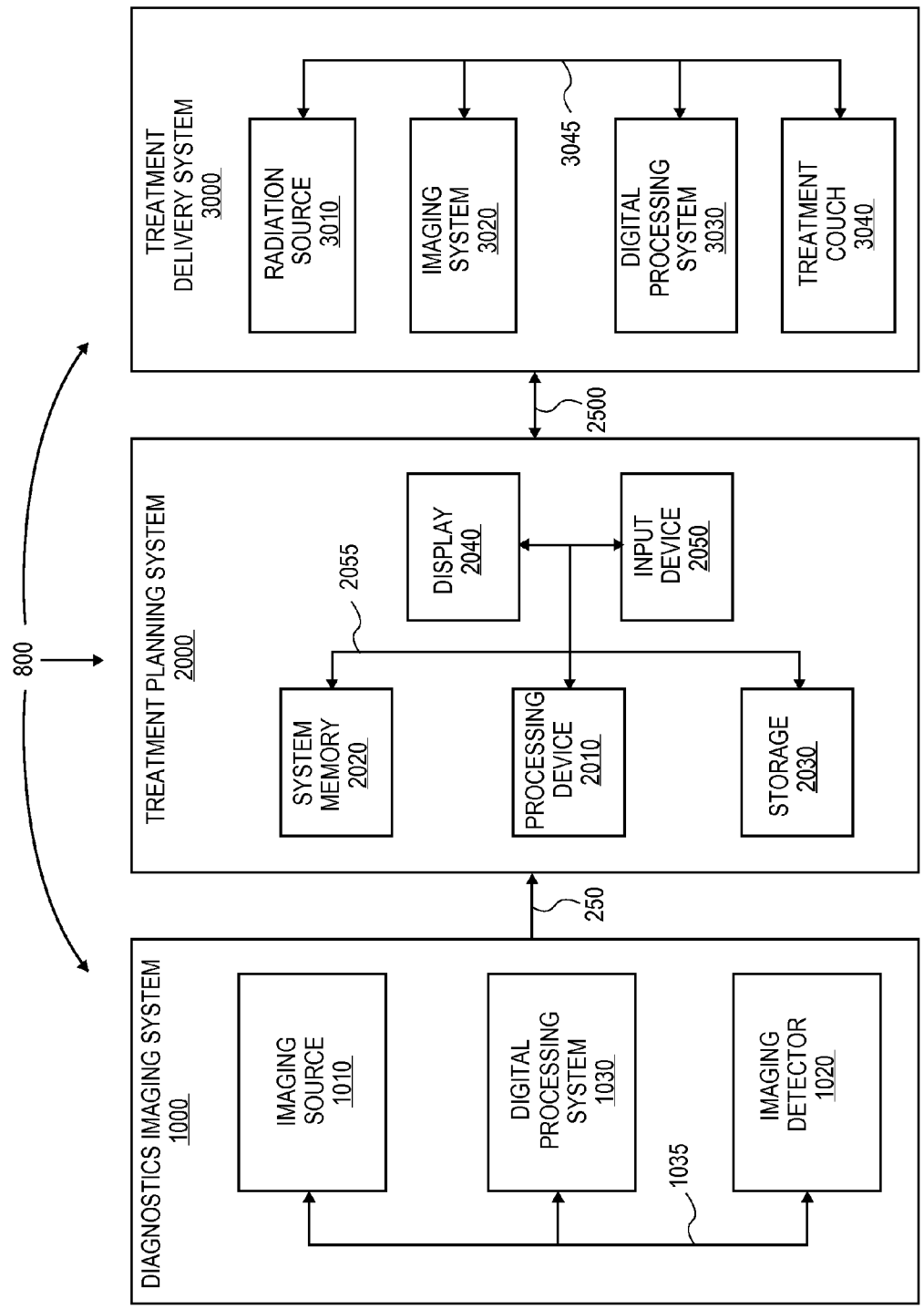
FIG. 8 is a block diagram illustrating a system that may implement embodiments of the present invention.

FIG. 8 illustrates a system 800 in which embodiments of the present invention may be implemented. As described below and illustrated in FIG. 8, system 800 may include a diagnostic imaging system 1000, a treatment planning system 2000 and a treatment delivery system 3000.

Diagnostic imaging system 1000 may be any system capable of producing medical diagnostic images of a patient that may be used for subsequent medical diagnosis, treatment planning and/or treatment delivery. For example, diagnostic imaging system 1000 may be an angiographic imaging system (e.g., system 100), a computed tomography (CT) system, a magnetic resonance imaging (MRI) system, a positron emission tomography (PET) system, an ultrasound system or the like.

Diagnostic imaging system 1000 includes an imaging source 1010 to generate an imaging beam (e.g., x-rays) and an imaging detector 1020 to detect and receive the beam generated by imaging source 1010. In one embodiment of the present invention, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments of the present invention, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data, such as angiographic imaging data and 3D scan data as described above. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning and/or image processing operations discussed herein, such as the spine segmentation tool described herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein and/or for storing 3D imaging data and DRRs as discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a digital processing system 3030 to control radiation source 3010, imaging system 3020 and a patient support device such as a treatment couch 3040. Digital processing system 3030 may be configured to register 2D radiographic images from imaging system 3020, from two or more stereoscopic projections, with digitally reconstructed radiographs (e.g., DRRs from segmented 3D imaging data) generated by digital processing system 1030 in diagnostic imaging system 1000 and/or DRRs generated by processing device 2010 in treatment planning system 2000. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement methods (e.g., such as method 1200 described above) to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more)

degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the AXUM® treatment couch, developed by Accuray Incorporated of Sunnyvale, Calif., or be another type of conventional treatment table known to those of ordinary skill in the art.

Alternatively, treatment delivery system 3000 may be another type of treatment delivery system, for example, a gantry based (isocentric) intensity modulated radiotherapy (IMRT) system. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment of the present invention, the gantry based system may have a gimbaled radiation source head assembly, where the gimbaled mechanism has two or more degrees of freedom. It should be noted that in embodiments of a gantry-based system, certain angles of the gantry will be known a-priori to block one of the imagers. For these gantry angels, the single image can be acquired and the quality assurance principles of tracking in image-guided procedures, as described herein, may be applied.

It should be noted that the methods and apparatus described herein are not limited to use only with medical diagnostic imaging and treatment. In alternative embodiments of the present invention, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Embodiments of the present invention include various operations, which are described herein. These operations may be performed by hardware components, software, firmware or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments of the present invention may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments of the present invention may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Although the operations of the method(s) herein are shown and described in a particular order, the order of the operations of each method may be altered so that certain operations may be performed in an inverse order or so that certain operation may be performed, at least in part, concurrently with other operations. In another embodiment of the present invention, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
aligning a volume of interest (VOI) in a three-dimensional (3D) treatment coordinate system with a reference position using imaging data;
monitoring alignment of the VOI in the 3D treatment coordinate system during a radiation treatment using monoscopic imaging data generated by a single imaging source;
detecting displacement of the VOI in the 3D treatment coordinate system using the monoscopic imaging data;
determining whether the displacement exceeds a displacement threshold; and
automatically modifying the radiation treatment if the displacement exceeds the displacement threshold.

2. The method of claim 1, further comprising:
acquiring stereoscopic imaging data if the displacement exceeds the displacement threshold; and
realigning the VOI in the 3D treatment coordinate system using the stereoscopic imaging data.

3. The method of claim 1, further comprising determining that the VOI can be realigned in the 3D treatment coordinate system using the monoscopic imaging data if the displacement does not exceed the displacement threshold.

4. The method of claim 3, further comprising realigning the VOI in the 3D treatment coordinate system using the monoscopic imaging data.

5. The method of claim 4, wherein the imaging data comprises two-dimensional (2D) projection images, and wherein aligning the VOI with the reference position comprises:
- acquiring first two-dimensional (2D) projection images of the VOI in each of two or more projections; and
- registering the first 2D projection images of the VOI in each of the two or more projections with 2D reference images of the VOI in each of the two or more projections, wherein the 2D reference images of the VOI are derived from 3D transformations of 3D scan data of the VOI.

6. The method of claim 5, wherein the registering comprises:
- comparing the first 2D projection images in each of the two or more projections with the 2D reference images in each of the two or more projections;
- determining a first similarity measure between the first 2D projection image in each of the two or more projections and selected 2D reference images in each of the two or more projections; and
- finding a first 3D transformation between a coordinate system of the VOI and a coordinate system of the 3D scan data of the VOI that maximizes the first similarity measure, wherein the first 3D transformation maps voxels in the coordinate system of the VOI to corresponding voxels in the coordinate system of the 3D scan data of the VOI.

7. The method of claim 6, wherein aligning the VOI with the reference position comprises at least one of moving the VOI through an inverse of the first 3D transformation and positioning a treatment source to compensate for the first 3D transformation.

8. The method of claim 6, wherein monitoring the alignment of the VOI in the 3D treatment coordinate system comprises:
- acquiring a second 2D projection image of the VOI in one of the two or more projections; and
- comparing the second 2D projection image with a selected 2D reference image of the VOI in the one of the two or more projections.

9. The method of claim 8, wherein detecting the movement of the VOI comprises:
- determining a second similarity measure between the second 2D projection image of the VOI and the selected 2D reference image of the VOI in the one of the two or more projections; and
- comparing the second similarity measure to the first similarity measure.

10. The method of claim 9, wherein detecting the movement of the VOI further comprises finding a second 3D transformation of the 3D scan data that maximizes the second similarity measure.

11. The method of claim 10, wherein realigning the VOI in the 3D treatment coordinate system comprises moving the VOI through an inverse of the second 3D transformation.

12. The method of claim 10, wherein realigning the VOI in the 3D treatment coordinate system comprises positioning a treatment source to compensate for the second 3D transformation.

13. The method of claim 10, wherein a difference between the second similarity measure and the first similarity measure is less than a critical value, the method further comprising continuing a radiation treatment procedure based on the 3D transformation between the coordinate system of the VOI and the coordinate system of the 3D scan data of the VOI.

14. The method of claim 10, wherein a difference between the second similarity measure and the first similarity measure is greater than or equal to a critical value, the method further comprising interrupting a radiation treatment procedure until the imaging data is available.

15. The method of claim 6, wherein monitoring the alignment of the VOI in the 3D treatment coordinate system comprises:
- acquiring a second 2D projection image of the VOI in one of the two or more projections; and
- comparing the second 2D projection image with a first 2D projection image of the VOI in the one of the two or more projections.

16. A treatment delivery system, comprising:
- a positioning system to position a volume of interest (VOI);
- an imaging system configured to acquire images of the VOI; and
- a processing device to control the imaging system and the positioning system, wherein the processing device is configured to:
  - align the VOI with a reference position in a three-dimensional (3D) treatment coordinate system using the images;
  - monitor alignment of the VOI in the 3D treatment coordinate system during a radiation treatment using monoscopic imaging data generated by a single imaging source;
  - detect displacement of the VOI in the 3D treatment coordinate system using the monoscopic imaging data;
  - determine whether the displacement exceeds a displacement threshold; and
  - automatically modify the radiation treatment if the displacement exceeds the displacement threshold.

17. The treatment delivery system of claim 16, wherein the processing device is further configured to detect movement of the VOI in the 3D treatment coordinate system using the monoscopic imaging data.

18. The treatment delivery system of claim 17, wherein the processing device is further configured to determine if the VOI can be realigned in the 3D treatment coordinate system using the monoscopic imaging data.

19. The treatment delivery system of claim 17, wherein the processing device is further configured to use the monoscopic imaging data to control the positioning system to realign the VOI in the 3D treatment coordinate system.

20. The treatment delivery system of claim 17, where the positioning system comprises a robotic positioning system having five or more degrees of freedom.

21. The treatment delivery system of claim 17, further comprising a radiation treatment source controlled by the processing device, wherein the processing device is configured to use the monoscopic imaging data to position the radiation treatment source to compensate for the displacement of the VOI.

22. An article of manufacture, comprising a non-transitory computer-readable medium including instructions that, when executed by a computer, cause the computer to perform operations comprising:
- aligning a volume of interest (VOI) in a three-dimensional (3D) treatment coordinate system with a reference position using imaging data;
- monitoring alignment of the VOI in the 3D treatment coordinate system during a radiation treatment using monoscopic imaging data generated by a single imaging source;
- detecting displacement of the VOI in the 3D treatment coordinate system using the monoscopic imaging data;
- determining whether the displacement exceeds a displacement threshold; and automatically modifying the radiation treatment if the displacement exceeds the displacement threshold.

23. The article of manufacture of claim 22, wherein aligning the VOI with the reference position comprises:
acquiring first two-dimensional (2D) projection images of the VOI in each of two or more projections; and
registering the first 2D projection images of the VOI in each of the two or more projections with 2D reference images of the VOI in each of the two or more projections, wherein the 2D reference images of the VOI are derived from 3D transformations of 3D scan data of the VOI, wherein registering comprises:
comparing the first 2D projection image in each of the two or more projections with the 2D reference images in each of the two or more projections;
determining a first similarity measure between the first 2D projection image in each of the two or more projections and selected 2D reference images in each of the two or more projections; and
finding a first 3D transformation between a coordinate system of the VOI and a coordinate system of the 3D scan data of the VOI that maximizes the first similarity measure, wherein the first 3D transformation maps voxels in the coordinate system of the VOI to corresponding voxels in the coordinate system of the 3D scan data of the VOI.

24. The article of manufacture of claim 23, wherein aligning the VOI with the reference position comprises moving the VOI through an inverse of the first 3D transformation or positioning a treatment source to compensate for the first 3D transformation.

25. The article of manufacture of claim 23, wherein monitoring the alignment of the VOI in the 3D treatment coordinate system comprises:
acquiring a second 2D projection image of the VOI in one of the two or more projections; and
comparing the second 2D projection image with a selected 2D reference image of the VOI in the one of the two or more projections.

26. The article of manufacture of claim 25, wherein detecting the movement of the VOI comprises:
determining a second similarity measure between the second 2D projection image of the VOI and the selected 2D reference image of the VOI in the one of the two or more projections; and
comparing the second similarity measure to the first similarity measure.

27. The article of manufacture of claim 25, wherein detecting the movement of the VOI further comprises finding a second 3D transformation of the 3D scan data that maximizes the second similarity measure.

28. The article of manufacture of claim 27, further comprising:
realigning the VOI in the 3D treatment coordinate system using the monoscopic imaging data, wherein realigning the VOI in the 3D treatment coordinate system comprises either moving the VOI through an inverse of the second 3D transformation, or positioning a treatment source to compensate for the second 3D transformation.

29. An apparatus, comprising:
means for aligning a volume of interest in a 3D coordinate system with a reference position using imaging data; and
means for monitoring alignment of the volume of interest during a radiation treatment using monoscopic imaging data generated by a single imaging source;
means for detecting displacement of the VOI in the 3D treatment coordinate system using the monoscopic imaging data;
means for determining whether the displacement exceeds a displacement threshold; and
means for automatically modifying the radiation treatment if the displacement exceeds the displacement threshold.

30. The apparatus of claim 29, further comprising means for realigning the VOI in the 3D treatment coordinate system using the monoscopic imaging data.

* * * * *